United States Patent [19]

Saito et al.

[11] 4,039,259
[45] Aug. 2, 1977

[54] EGG INSPECTING APPARATUS

[75] Inventors: Hisatoshi Saito, Yokohama; Kuniyoshi Kimura, Iwakura, both of Japan

[73] Assignee: Kewpie Kabushiki Kaisha, Japan

[21] Appl. No.: 632,063

[22] Filed: Nov. 14, 1975

[30] Foreign Application Priority Data

Nov. 18, 1974 Japan .................. 49-132579
Sept. 19, 1975 Japan .................. 50-113415
Sept. 19, 1975 Japan .................. 50-113416

[51] Int. Cl.² ........................................ G01N 33/08
[52] U.S. Cl. ........................ 356/53; 356/205; 356/208
[58] Field of Search .......................... 356/51-53, 356/36, 205-206, 208; 250/461, 565, 568

[56] References Cited

U.S. PATENT DOCUMENTS

| | | | |
|---|---|---|---|
| 3,130,255 | 4/1964 | Blackburn et al. | 356/53 |
| 3,255,660 | 6/1966 | Hirt | 250/207 |
| 3,492,073 | 1/1970 | Michael | 356/53 |
| 3,781,112 | 12/1973 | Groner et al. | 250/565 |
| 3,787,124 | 1/1974 | Lowy et al. | 250/565 |
| 3,920,334 | 11/1975 | Steichen et al. | 356/205 |

FOREIGN PATENT DOCUMENTS 696,675   9/1953   United Kingdom .............. 356/208

*Primary Examiner*—John K. Corbin
*Assistant Examiner*—Wm. H. Punter
*Attorney, Agent, or Firm*—Oblon, Fisher, Spivak, McClelland & Maier

[57] ABSTRACT

An egg inspecting apparatus operating to apply different lights necessary for detecting blood-containing eggs, addled or turbid eggs and eggs affected with bacteria to an egg to be inspected, to subject lights from the egg to photo-electric conversion to obtain electrical signals, and to detect the levels of these electrical signals so as to determine whether or not the egg is inferior or defective.

2 Claims, 14 Drawing Figures

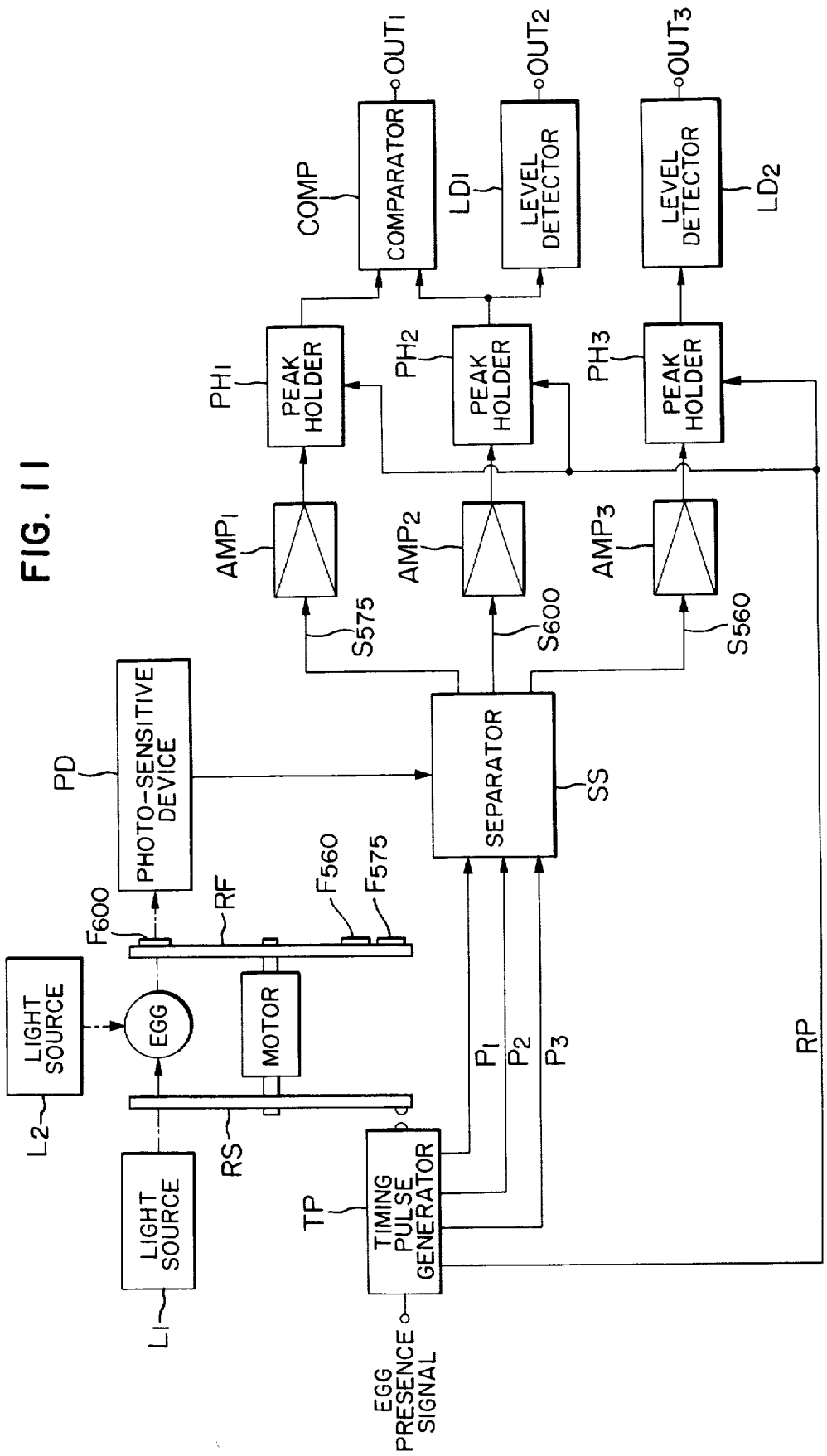

EGG INSPECTING APPARATUS

BACKGROUND OF THE INVENTION

This invention relates to egg inspecting apparatuses with which inferior or defective eggs can be detected without breaking the eggs.

In conventional egg inspecting apparatuses operating to detect blood-containing eggs (hereinafter referred to as "blood eggs" when applicable), a light having a wavelength of 575 mμ (hereinafter referred to as "a 575 mμ light or an absorptive light" when applicable) which is appreciably absorbed by blood and a light having a wavelength of 600 mμ (hereinafter referred to as "a 600 mμ light or a non-absorptive light" when applicable) which are not appreciably absorbed by blood are applied to an egg to be inspected, and the two lights transmitted through the egg are compared with each other to determine the presence or absence of blood in the egg.

However, it is not logical to determine the presence or absence of blood merely by comparing the intensities of the two lights transmitted through the egg, because the intensities of light transmitted through eggs vary depending on the optical properties of the eggs such as the variations in thickness and color of the shells thereof. In order to solve this problem, in the conventional egg inspecting apparatus, the level of a light detection signal obtained by detecting the 600 mμ light transmitted through an egg is maintained fixed irrespective of the optical property of the egg, and the level of a light detection signal obtained by detecting the 575 mμ light passed through the egg is determined relative to the level of the 600 mμ light thus maintained fixed, thereby determining the presence or absence of blood in the egg.

For this purpose, photomultipliers are provided respectively for receiving the absorptive light and the non-absorptive light, and the level of the detection signal of the photomultipler provided for non-absorptive light is maintained fixed by the use of a compensation circuit. On the basis of the level of the detection signal thus maintained fixed, the level of the detection signal of the photomultipler tube provided for the absorptive light is determined. Since the photomultiplier tube has higher sensitivity than other photosensitive elements, it is advantageous in that, for instance, the provision of an amplifier is unnecessary, and the intensity of a light source may be lower.

However, the photomultiplier tube has an inherent difficulty in that its linearity range is small. A sensitivity characteristic of the photomultiplier tube is as indicated by the solid line FIG. 1, and therefore in the inspection of eggs with brown shells (hereinafter referred to as "brown eggs" when applicable) the sensitivity of the photomultiplier tube should be increased as indicated by the broken line in FIG. 1. Under this condition, the outputs of the photomultiplier tube produced by lights $L_1$ and $L_2$ in the inspection of a normal egg with a white shell and an egg containing a slight amount of blood fall within the saturation range of the characteristic curve indicated by the broken line, and, therefore, it is impossible to detect even blood eggs. In order to solve this problem, a compensation circuit is provided in the conventional egg inspecting apparatus in such a manner that the sensitivity of the photomultipler tube where the intensity of a light passed through an egg is high, that is, where a light passed through a normal egg with white shell falls in the linearity range.

Defective eggs include so-called "green eggs" which are eggs affected with bacteria as well as blood eggs, addled eggs and turbid eggs which can be detected by the use of visible light as was described above. The bacteria are regarded to be low-temperature bacteria such as "pseudomonas fluorescenes". When such bacteria have propagated in an egg, the albumen of the egg can be visually observed to be green. However, when the propagation of bacteria in an egg is slight, it is impossible to visually detect whether or not the eggis affected with the bacteria even if the egg is broken.

The bacteria described above are not poisonous and are not bacilli but are well known as decomposing bacteria. It has been determined in the United States of America and also Japan that green eggs are not fit for use as food.

However, conventional green eggs detection methods are applicable only to eggs in which the propagation of bacteria has advanced remarkably. Accordingly, there has been a strong demand for the provision of an egg inspecting apparatus capable of positively detecting not only eggs in which the degree in propagation of bacteria is remarkable, but also eggs in which the degree in propagation of bacteria is slight.

As is apparent from the above description, the conventional egg inspecting apparatuses are directed only to the detection of blood eggs, and addled or turbid eggs originated from blood, or only to green eggs. That is, heretofore, there has been no egg inspecting apparatus which can quickly and positively detect all of the defective eggs including blood eggs, addled or turbid eggs, and green eggs.

SUMMARY OF THE INVENTION

Accordingly, an object of this invention is to provide an egg inspecting apparatus in which all of the above-described difficulties accompanying conventional egg inspecting apparatuses are overcome.

More specifically, a first object of this invention is to provide an egg inspecting apparatus having a photosensitive device of a linearity range which is relatively wide, thereby eliminating the compensation circuit provided in a conventional egg inspecting apparatus.

A second object of the invention is to provide an egg inspecting apparatus which is stably operable for a relatively long period of time.

A third object of the invention is to provide an egg inspecting apparatus which can quickly and positively detect blood-containing eggs and addled or turbid eggs originated from blood contained therein without breaking the eggs.

A fourth object of the invention is to provide an egg inspecting apparatus which can detect not only eggs affected seriously with bacteria but also eggs affected slightly with bacteria without breaking the eggs.

A fifth object of the invention is to provide an egg inspecting apparatus which can readily detect all defective eggs including blood-containing eggs, addled eggs, turbid eggs, and eggs affected with bacteria.

A sixth object of the invention is to provide an egg inspecting apparatus which has a simple construction.

The manner in which the foregoing objects and other objects are achieved by this invention will become more apparent from the following detailed description and the appended claims when read in conjunction with the accompanying drawings, in which like parts are designated by like reference characters.

BRIEF DESCRIPTION OF THE DRAWINGS

In the accompanying drawings:

FIG. 11 is a block diagram illustrating the combined relationship between the optical and electrical systems of the egg inspecting apparatus shown in FIG. 9;

DETAILED DESCRIPTION OF THE INVENTION

A first example of an egg inspecting apparatus according to this invention operates to detect eggs containing blood (hereinafter referred to as "blood eggs" when applicable) and also addled or turbid eggs (hereinafter referred to as "black eggs" when applicable) originating from blood eggs.

Figure 1:
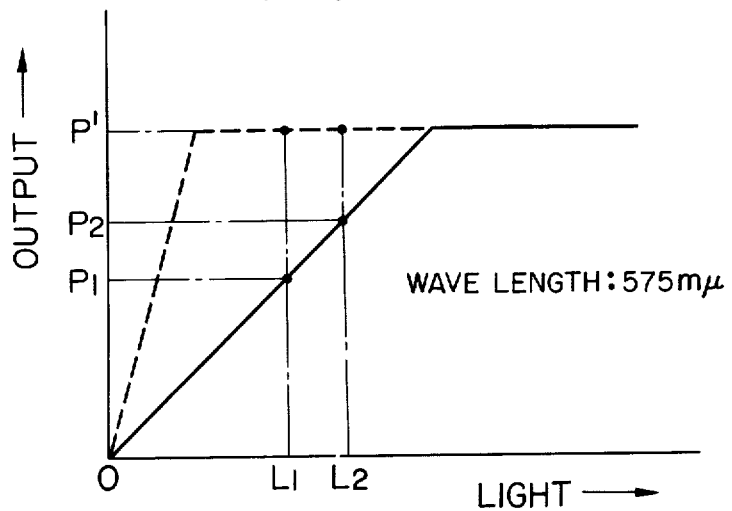
FIG. 1 is a graphical representation indicating an optical response characteristic curve of a photomultiplier tube.
Figure 2:
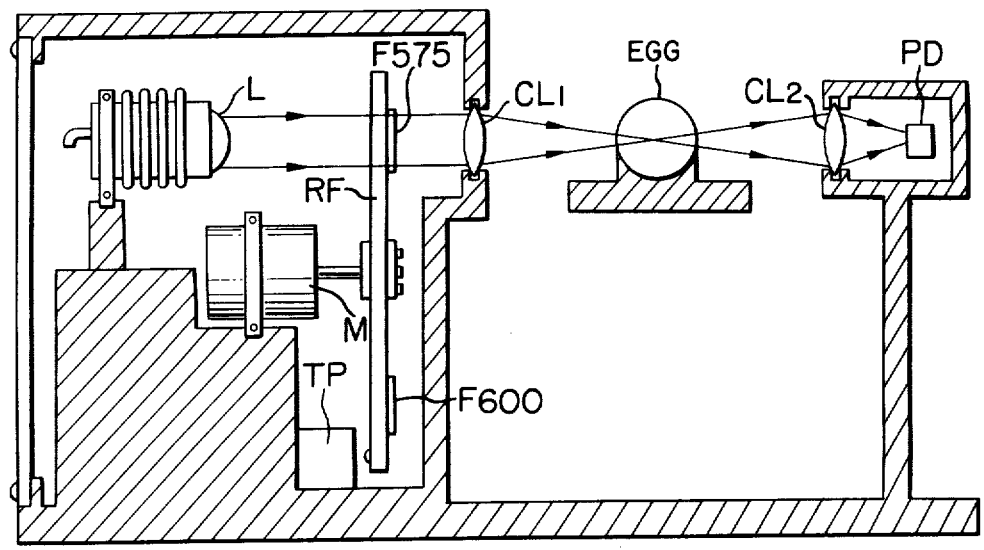
FIG. 2 is an explanatory diagram illustrating the arrangement of a first example of an egg inspecting apparatus according to this invention.

This egg inspecting apparatus as shown in FIG. 2 comprises a light source L provided in a dark chamber, a first condensing lens $CL_1$ fitted in an opening of the dark chamber, a second condensing lens $CL_2$ set apart from the first condensing lens $CL_1$, and a photo-sensitive device PD confronting the second condensing lens $CL_2$. Light beams emitted from the light source L are condensed by the first condensing lens $CL_1$ and then applied to the device PD through the second condensing lens $CL_2$. An egg to be detected is placed at an egg inspection point in the light path between the two condensing lens $CL_1$ and $CL_2$.

In order to apply two different lights, that is, the absorptive light and the non-absorptive light described before to the egg a rotating filter plate RF is provided between the light source L and the first condensing lens $CL_1$. The rotating filter plate RF is provided with two filters F575 and F600 and is rotated by an electric motor M. The filter F575 passes a light having a wavelength of 575 m$\mu$ (hereinafter referred to as a 575 m$\mu$ light), while the filter F600 passes a light having a wavelength of 600 m$\mu$ (hereinafter referred to as a 600 m$\mu$ light when applicable). Thus, the 575 m$\mu$ light and the 600 m$\mu$ light alternately and intermittently appear on the light path. Accordingly, if a rotational position of the rotating filter plate RF is detected to produce a position detection signal, these 575 m$\mu$ light and 600 m$\mu$ light can be separated on the basis of the relationships between the position detection signal and the light detection signal produced by the photosensitive device PD. In order to facilitate this function, a timing pulse generator TP is utilized.

Figure 3:
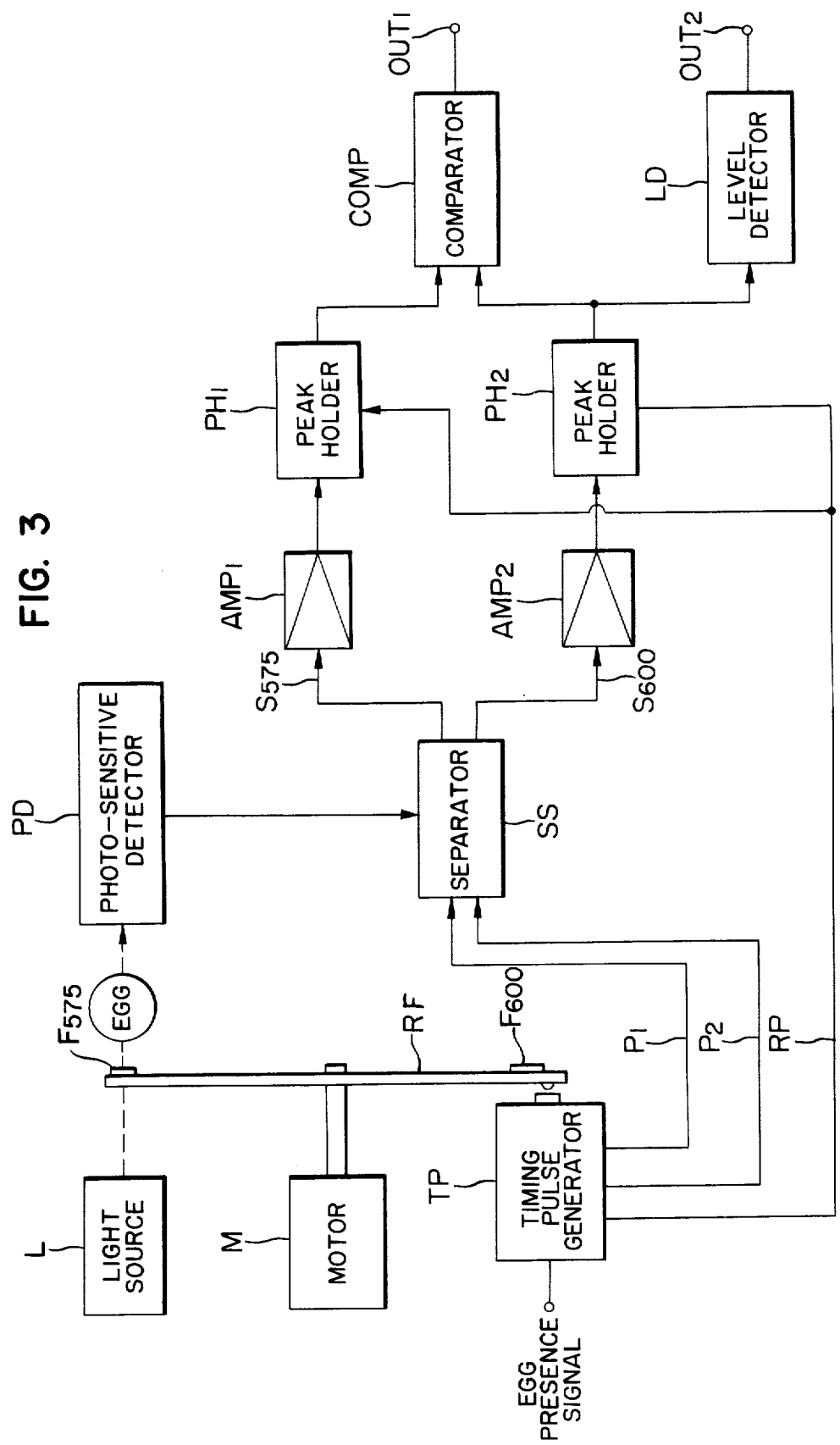
FIG. 3 is a block diagram illustrating the combined relationship between the optical and electrical systems of the an egg inspecting apparatus shown in FIG. 2.

FIG. 3 is a block diagram illustrating the optical and electrical systems, in combination, of the egg inspecting apparatus shown in FIG. 2. When the filter plate RF is rotated, with an egg to be inspected disposed at the egg inspection point, the 575 m$\mu$ light and the 600 m$\mu$light are alternately obtained through the filters F575 and F600 of the rotating filter plate RF and are applied to the photo-sensitive device PD through the egg, whereby respective light detection signals are produced by the photo-sensitive device PD. The light detection signals thus produced are then applied to a synchronization type separator SS in a signal processing section comprising the separator SS, amplifiers $AMP_1$ and $AMP_2$, peak holders $PH_1$ and $PH_2$, a comparator COMP and a level detector LD, while timing signals $P_1$ and $P_2$ generated by the timing pulse generator TP in synchronization with the rotating filter plate RF are applied to the separator SS.

If in this operation, a light detection signal is produced by the device PD for the 575 m$\mu$ light when the timing pulse $P_1$ is produced, a detection signal produced by the device PD when the timing signal $P_2$ is produced is for the 600 m$\mu$ light. Thus, signal separation is carried out, that is, a signal $S_{575}$ representative of the 575 m$\mu$ light and a signal $S_{600}$ representative of the 600 m$\mu$ light are separately produced by the synchronization type separator SS. These signals $S_{575}$ and $S_{600}$ thus obtained are amplified by the amplifiers $AMP_1$ and $AMP_2$ and applied to the peak holders $PH_1$ and $PH_2$, respectively.

The peak holders $PH_1$ and $PH_2$ operate to store values corresponding to the peak values of the signals $S_{575}$ and $S_{600}$, respectively, and to apply their outputs to the comparator COMP, in which the output of the peak holder $PH_1$ is compared with that of the peak holder $PH_2$. When the level of the output of the peak holder $PH_1$ is greater than a predetermined value with respect to the level of the output of peak holder $PH_2$, no output signal is produced by the comparator COMP, but when it is smaller, an output signal is produced at the output terminal $OUT_1$ of the comparator COMP. That is, the fact that the intensity of the absorptive light is lower to a certain degree when compared with that of the non-absorptive light means that the egg inspected is a blood egg. Therefore, the output at the output terminal $OUT_1$ is introduced into a mechanism (not shown) to segregate the blood egg from other normal eggs.

Described above is a case where the comparator COMP produces output signals to segregate blood eggs. However, the comparator COMP may produce outputs when eggs to be inspected are not blood eggs. More specifically, there is a possibility of a case in which the egg is normal, but only the signal representative of the non-absorptive light is applied to the photosensitive device PD (the signal representative of the absorptive light being not applied thereto) depending on the rotational condition of the filter plate RF. This phenomenon is the same as that in a case where the absorptive light is absorbed by a blood egg. However, the egg is a normal egg and should not be rejected.

In order to solve this problem, the output of the comparator COMP is kept locked for a certain period of time, or until two inputs described before are applied to the comparator COMP. In addition, a gate circuit (not shown) is provided between the output of the comparator COMP and its output terminal $OUT_1$. The gate circuit thus provided is controlled by a timer (not shown) in a manner such that an output produced by the photo-sensitive device PD upon reception of one of the absorptive and non-absorptive lights is used to start the operation of the timer. Then, at a time instant when the photo-sensitive device PD is supposed to receive the other light, a gate opening signal applied from the timer to the gate circuit. In order to close the gate circuit, a reset pulse RP generated by the timing pulse generator TP can be employed.

The output of the peak holder $PH_2$ is further applied to the level detector LD. When the level of the output applied to the level detector LD is less than a predetermined value, the latter LD produces an output. That is, the fact that the intensity of the non-absorptive light is less than a predetermined value means that the egg inspected is an addled egg, or a so-called black egg which must be rejected also.

Thereafter, a reset pulse RP is applied to the peak holders $PH_1$ and $PH_2$ by the timing pulse generator TP to reset the peak holders, that is, to remove the contents stored therein. Thus, the egg inspecting apparatus becomes ready for the inspection of the succeeding egg.

There is a case where an egg to be inspected is not placed at the egg inspection point although a light has been applied to the optical detector by the rotation of the rotating filter R. In this case, a special signal indicating that an egg is at the egg inspection point is not applied to the timing pulse generator TP, which therefore does not produce the timing pulses $P_1$ and $P_2$, and the synchronization type separator SS does not operate.

Figure 4:
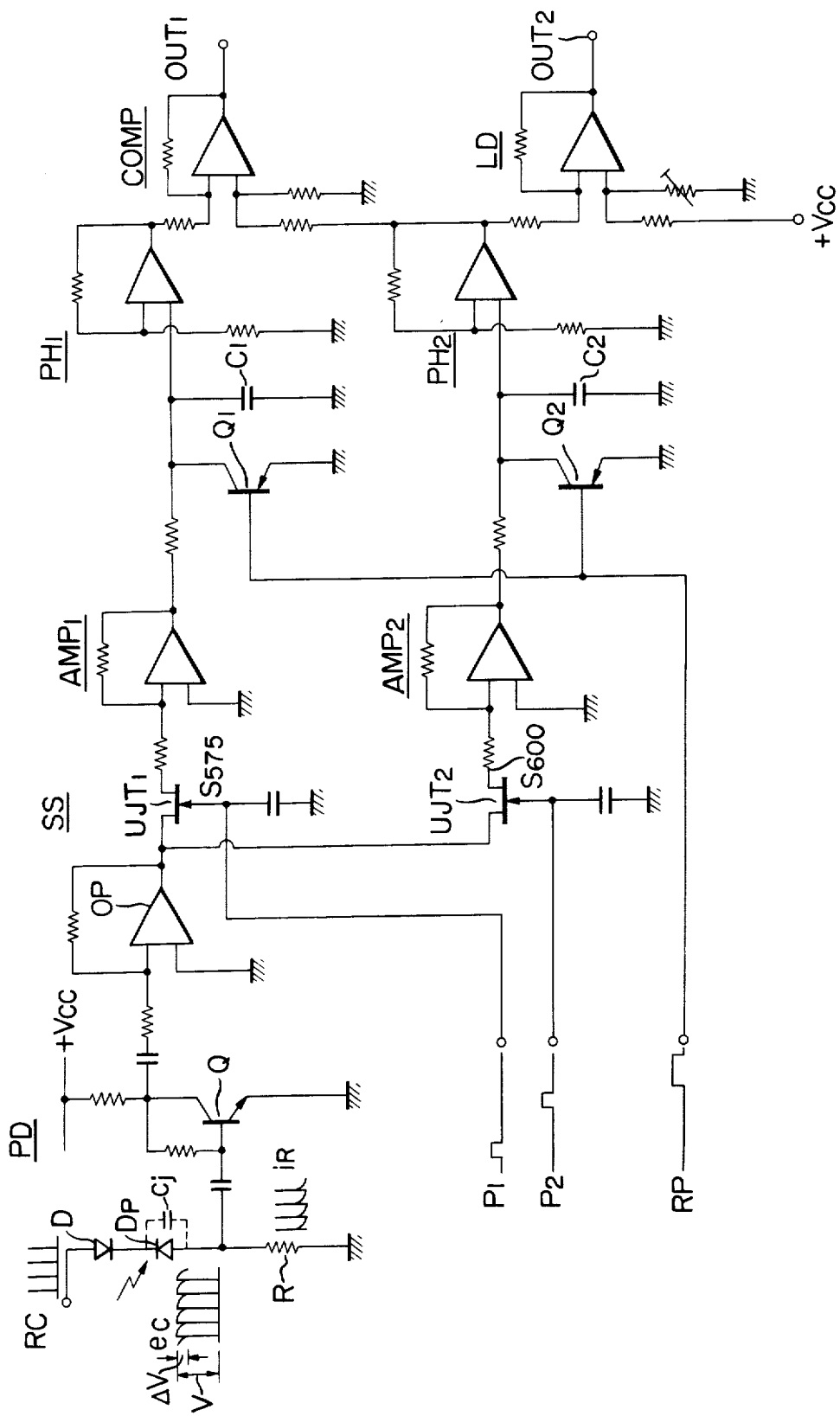
FIG. 4 is an electrical circuit diagram of the egg inspecting apparatus shown in FIG. 2.

FIG. 4 is an electrical circuit diagram illustrating in detail the egg inspecting apparatus shown in FIG. 3 except for the timing pulse generator TP. The operation of the photo-sensitive device PD is carried out by the use of a photo-sensitive element having an electric charge storing effect as was described before. The photo-sensitive device PD comprises a series circuit formed by series-connecting a diode D and a photo-diode Dp back to back or in such a manner that the anode of the diode D is connected to that of the photo-diode Dp, and by connecting a resistor R to the cathode of the photo-diode *Dp*.

A read clock pulse RC is applied to the series circuit thus formed to charge the junction capacitance $Cj$ of the photo-diode Dp, and then the light is applied to the photo-diode Dp through an egg to be inspected. In this operation, the junction capacitance $Cj$ is charged with a voltage V at a time instant when the first read clock pulse RC is applied to the series circuit, but is discharged for a period of time from that time instant to a time instant when the second read clock pulse RC is applied thereto. As a result, a charge voltage ec of the junction capacitance $Cj$ slightly drops by a voltage $\Delta V$. Then, the junction capacitance $Cj$ is charged by the voltage drop $\Delta V$ by the third read clock pulse RC, and simultaneously a pulsive current $iR$ flows in the resistor R. The peak value this current depends on the intensity of light applied to the photo-diode Dp. Accordingly, a voltage $iR \cdot R$ is developed across the resistor R in response to the intensity of the light applied to the photo-diode Dp.

The voltage $iR \cdot R$ thus developed is amplified by a transistor Q and an operational amplifier OP, and is then applied to unijunction transistors $UJT_1$ and $UJT_2$ in the synchronization type separator SS. These unijunction transistors $UJT_1$ and $UJT_2$ operate as gate circuits. Application of a timing pulses $P_1$ (or $P_2$) to the emitter of the transistor $UJT_1$ (cr $UJT_2$) causes its circuit to open so as to introduce the output signal of the photo-sensitive device PD into an amplifier $AMP_1$ (or $AMP_2$). The application of the timing pulses is effected in synchronization with the rotation of the rotating filter plate so that the amplifier to which the output signal or voltage signal of the device PD is to be applied is selected in accordance with the wavelength of light transmitted through the egg. More specifically, when the wavelength of the light 575 m$\mu$, the voltage signal is applied to the amplifier $AMP_1$, while when it is 600 m$\mu$, the voltage signal is applied to the amplifier $AMP_2$.

The signal amplified by the amplifier $AMP_1$ (or $AMP_2$) is applied to the peak holder $PH_1$ (or $PH_2$) which comprises a hold circuit including a transistor $Q_1$ ($Q_2$). Each of the hold circuits stores the signal for a period of time during which the hold circuit is in a hold state. This hold state of the hold circuit is reset by the application of the reset pulse RP, that is, the hold circuit remains in the hold state for a period of time during which no reset pulse is applied thereto. Since, when the signal from the amplifier $AMP_1$ (or $AMP_2$) is applied to the peak holder $PH_1$ (or $PH_2$), no rest pulse RP is applied to the peak holder, the peak holder $PH_1$ (or $PH_2$) can store the signal and then apply it to the comparator COMP.

The comparator COMP operates to compare the output signal of the peak holder $PH_1$ with that of the peak holder $PH_2$. When the output signal of the peak holder $PH_1$ or the signal representative of the absorptive light transmitted through the egg is less than a predetermined value when compared with the output signal of the peak holder $PH_2$ or the signal representative of the non-absorptive light transmitted through the egg, the comparator produces an output signal at its output terminal $OUT_1$, which output signal is utilized for the rejection of a blood egg as was described before.

The output signal of the peak holder $PH_2$ is further applied to the level detector LD so as to determine whether or not the level of the non-absorptive light passed through the egg is lower than a predetermined value. If this level is lower than the predetermined value, the egg is a black egg and an output signal is produced by the level detector LD at its output terminal thereby to reject the black egg.

Figure 5:
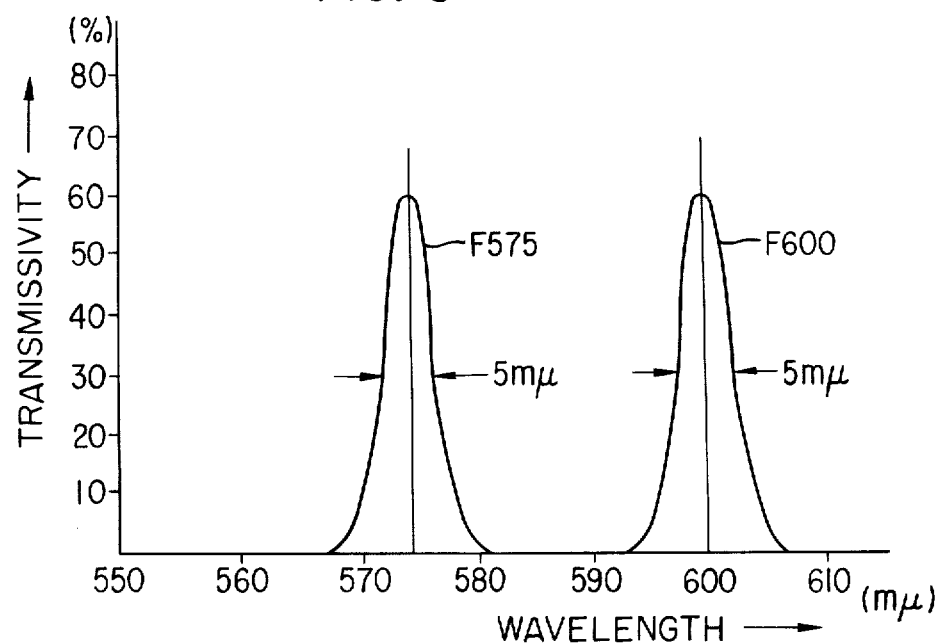
FIG. 5 is a graphical representation indicating the transmissivities of two filters employed in the egg inspecting apparatus shown in FIGS. 2, 3 and 4.

FIG. 5 is a graphical representation indicating the transmissivity characteristics of the filters F575 and F600 provided in the rotating filter plate RF.

Figure 6:
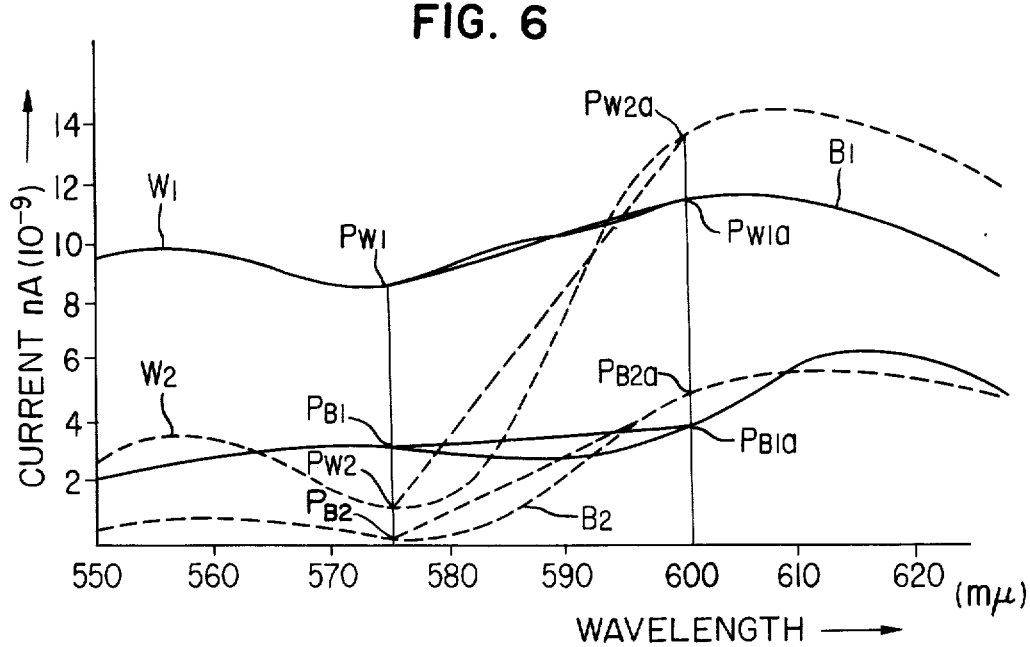
FIG. 6 is also a graphical representation indicating four current-wavelength characteristic curves obtained by inspecting a normal egg with a white shell, a blood containing egg with a white shell, a normal egg with a brown shell and a blood-containing egg with a brown shell.

FIG. 6 is a graphical representation indicating four current-wavelength characteristic curves $W_1$, $W_2$, $B_1$ and $B_2$ obtained respectively by inspecting a normal egg with a white shell, a blood egg with a white shell, a normal egg with a brown shell and a blood egg with a brown shell. As is apparent from the graphical representation, the curve $W_1$ of a normal egg with a white shell is clearly different from that $W_2$ of a blood egg with a white shell, and also the curve $B_1$ of a normal egg with a brown shell is significantly different from that $B_2$ of a blood egg with a brown shell, although the latter difference is not as clear as the former difference.

With the curve $W_1$ of a normal egg with a white shell, an output current at a point $PW_1$ corresponding to the wavelength of 575 m$\mu$ is 9 nA, and an output current at a point $PW_{1a}$ corresponding to the wavelength of 600 m$\mu$ is 11nA, that is, the difference between the two output currents is very slight. On the other hand, with the curve $W_2$ of a blood egg with a white shell, an output current at a point $PW_2$ corresponding to the wavelength of 575 m$\mu$ is 1 nA, and an output current at a point $PW_{2a}$ corresponding to the wavelength of 600 m$\mu$ is 14 nA, that is, the difference between the two output signals is great. This tendency exists in the inspection of eggs with brown shells also. Therefore, blood eggs can be positively rejected.

Defective eggs include not only blood-containing eggs but also addled eggs and turbid eggs. Since the primary cause of these addled or turbid eggs is blood contained therein, the egg inspecting apparatus described above is effective for rejecting such addled or turbid eggs.

In the example of this invention described above, the absorptive light and the non-absorptive light are both applied to one and the same photo-sensitive device, and the distribution of the signals representative of these lights is effected with the aid of timing means. However, the separation of the two lights and accordingly the distribution of the signals may be achieved by providing two photo-sensitive devices so as to receive the two lights, respectively. In this case, the light source L may be replaced by a light source which emits a mixed light of the absorptive light and the non-absorptive light.

Furthermore, in the example described above, the 575 m$\mu$ light and the 600 m$\mu$ light are employed for the rejection of defective eggs since these two lights are most suitable with respect to the optical transmission characteristics of eggs. However, lights of other wavelengths may be employed for the same purpose.

The photo-diode in the photo-sensitive device PD may be replaced by a photo-transistor or a solar battery.

In the example of the present invention, the absorptive light and the non-absorptive light passed through an egg to be inspected are received by the photo-sensitive element having an electric charge storing effect as was described above. Therefore, the linearity range of the egg inspecting apparatus is much greater than that of the conventional egg inspecting apparatus employing a photomultiplier tube, and accordingly no compensation circuit is necessary in the apparatus of this invention. Furthermore, since no photomultiplier tube is employed in the apparatus of the invention, no problems due to the short service life and great variation with time of the photomultiplier tube are involved in the apparatus. That is, the egg inspecting apparatus according to the invention can operate stably for a long period of time.

In the case where the absorptive light and the nonabsorptive light are applied to an egg at different time instants, the detection of the lights can be achieved by the provision of only one photo-sensitive device. Furthermore, in the case where two photo-sensitive devices are provided for the detection of the two lights, respectively, the constructions of the light emitting section and the light detection signal processing section can be made simple when compared with the above case.

In addition, in the case where only the non-absorptive light is detected, not only blood eggs but also black eggs can be detected.

According to another aspect of this invention, an egg inspecting apparatus is provided, as a second example of the invention, which can detect green eggs.

Figure 7:
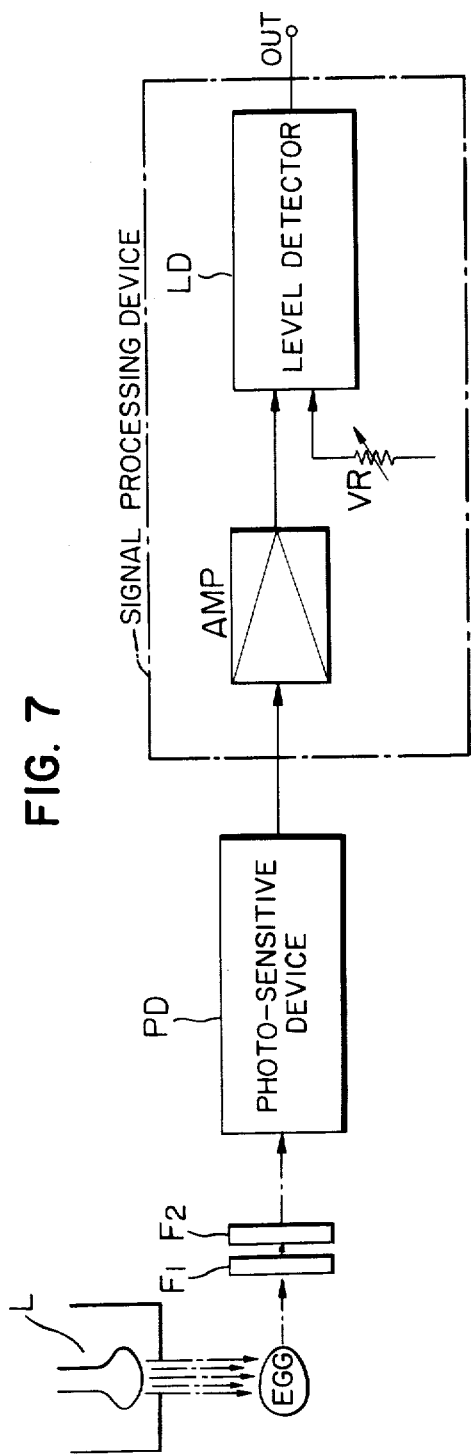
FIG. 7 is a block diagram illustrating the combined relationship between the optical and electrical systems of a second example of the egg inspecting apparatus according to the invention.

This apparatus, as shown in FIG. 7, comprises a light source L emitting what is a so-called "black light" or near-ultraviolet light, filters $F_1$ and $F_2$ and a signal processing device including a photo-sensitive device PD, an amplifier AMP, and a level detector LD.

The light source L is enclosed in a dark chamber and is adapted to emit rays near ultraviolet through a slit provided in a wall of the dark chamber so that the near-ultraviolet rays are focussed on the shell of an egg to be inspected. The photosensitive device PD, being arranged perpendicularly to the direction of the near-ultraviolet rays emitted, receives light from the egg through the two filters $F_1$ and $F_2$. In this operation, the filters $F_1$ and $F_2$ serve to remove ultraviolet rays from the light from the egg, that is, the filters operate to apply only a visible light to the photo-sensitive device PD.

The device PD may be constituted by a photomultiplier tube, a photo-diode, a photo-transistor, or a solar battery.

The output or light detection signal of the photo-sensitive device PD is applied to the level detector LD through the amplifier AMP, and is compared with a reference signal preset by a reference-signal-setting device VR so as to determine whether or not the egg is a green egg.

The principle of this apparatus is based on the fluorescence of green eggs. Upon application of the near-ultraviolet light, the shell of a normal egg appears to be dark violet while the shell of a green egg appears to be white. Thus, the detection of a green egg can be achieved by determining whether or not an egg irradiated by the near-ultraviolet light appears to be white.

In this connection, it is known that a near-ultraviolet light having a wavelength of 384 m$\mu$ is most suitable for the detection of green eggs, and that a near-ultraviolet light having a wavelength of 384±5 m$\mu$ is practical for the same purpose.

As was described above, when the near ultraviolet light is applied to a green egg, it appears to be white. Therefore, ultraviolet light having a wavelength less than 400 m$\mu$ produced when the near-ultraviolet light is irregularly reflected by the surface of the green egg, must be removed by the filters so as to prevent erroneous light detection of the photo-sensitive device PD.

Figure 8:
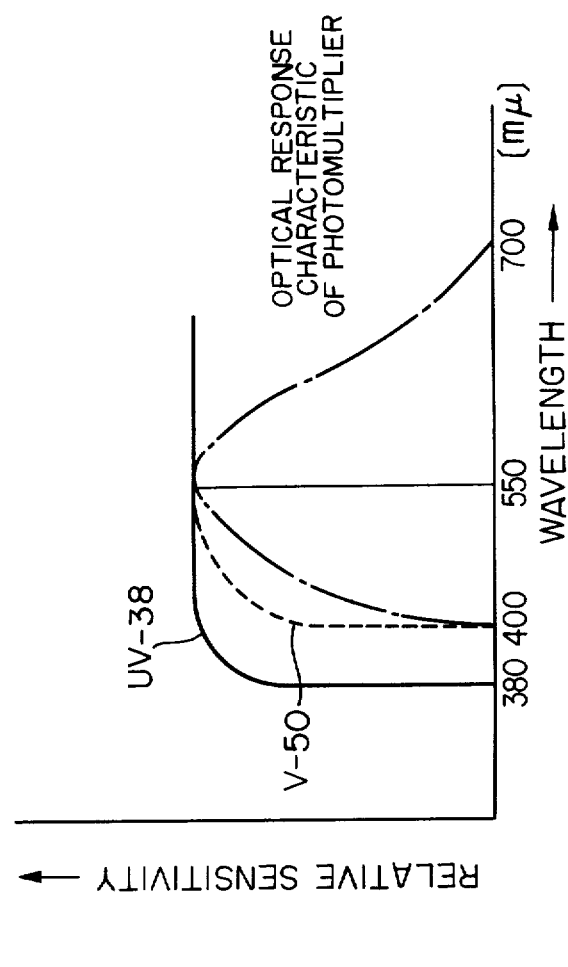
FIG. 8 is a graphical representation indicating optical response characteristics of two filters employed in the egg inspecting apparatus shown in FIG. 7 and that of a photomultiplier also employed in the same.

FIG. 8 is a graphical representation indicating the optical response characteristic curves of the photomultiplier tube and the filters employed in the apparatus shown in FIG. 7. Two filters UV-38 and Y-50 are employed as the filters $F_1$ and $F_2$. Since the use of only one filter UV-38 is inadequate to thoroughly eliminate the ultraviolet light, the filter Y-50 is additionally used.

As is apparent from FIG. 7, the optical response characteristic curve of the photomultiplier tube has its peak sensitivity value with a light of approximately 550 mμ is wavelength, that is, the sensitivity of the photomultiplier tube is reduced with lights of wavelengths less than and more than 550 mμ. According to experiments, the ratio of the detection signal of a green egg to that of a normal egg corresponding to such peak value is 60:8 as a maximum and 41:18 as a minimum. Accordingly, green eggs can be detected merely by determining these detection outputs.

If it is required to detect green eggs slightly affected with bacteria, the detection output is applied to the level detector LD through the amplifier AMP. The level detector LD allows the detection signal amplified by the amplifier AMP to be compared with the reference signal set by the reference-signal-setting device VR.

As was described, with this apparatus it is determined whether or not an egg being inspected appears to be white when light having a wavelength of 384±5 mμ is applied thereto, and therefore green eggs can be positively detected.

Furthermore, in the apparatus shown in FIG. 7, near-ultraviolet light is applied to an egg to be inspected, and light from the egg is introduced to the photo-sensitive device through the filters blocking ultraviolet light. Accordingly, it can be determined from the output of the signal processing device whether or not the egg under inspection is a green egg. Thus, the detection of green eggs can be readily achieved.

According to another aspect of this invention, an egg inspecting apparatus which can detect not only blood eggs and black eggs but also green eggs which are affected with bacteria, as was described before is provided.

This apparatus includes the same parts as those of the first embodiment (FIGS. 3 and 4) of the invention as will become apparent later. Such parts will be described briefly when applicable.

Figure 9:
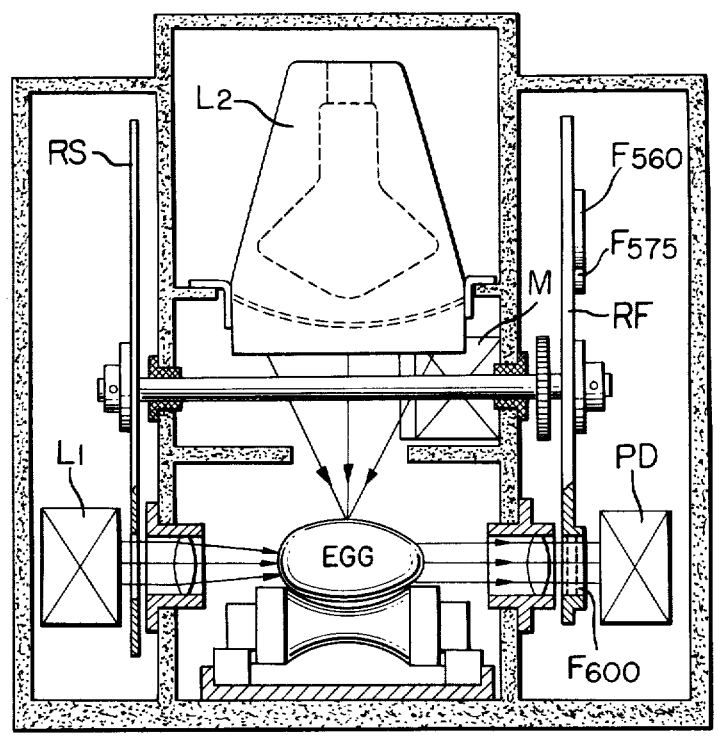
FIG. 9 is an explanatory diagram illustrating an arrangement of a third example of the egg inspecting apparatus according to invention.

The apparatus, as shown in FIG. 9, comprises a dark chamber surrounding a part of an egg-conveying device such as a conveyer. In the dark chamber there are provided two light sources $L_1$ and $L_2$, a rotating filter plate RF, an electric motor M, and a photo-sensitive device PD.

The light source $L_1$ covers a range of a wavelength of 575 mμ to a wavelength of 600 mμ but not the region of ultraviolet rays. An egg to be inspected, the light source $L_1$ and the photo-sensitive device PD are arranged on a straight line in such a manner that an egg inspection point is between the light source $L_1$ and the device PD. A rotating shutter RS is provided to intermittently shield a light projected toward the egg from the light source $L_1$. The rotating filter plate RF has optical filters which are adapted to selectively pass lights projected thereto to the photo-sensitive device PD as will become more apparent latter. The shutter RS and the filter plate RF are mounted on one and the same shaft which are rotated by the electrical motor M. The light source $L_2$ is adapted to emit near-ultraviolet rays and is positioned above the egg so that the near-ultraviolet rays are focussed on the shell of the egg.

The reason for employment of the light sources $L_1$ emitting a light having a wavelength range of 575 mμ to 600 mμ and also the light source $L_2$ emitting the near-ultraviolet rays is that it is impossible to carry out both inspection of blood eggs and black eggs and inspection of green eggs by the use of only one light source, that is, a light having the same wavelength. That is, the former inspection should be performed with a blood-sensitive wavelength light or a 575-mμ light, and a blood-nonsensitive wavelength light, or a 600-mμ light, while the latter inspection should be performed with a light having a wavelength of 384 or a 384 mμ light which causes a green egg to luminesce.

As was described before, a blood-containing egg can be detected by comparing the resultant intensity of the 575 mμ light transmitted through the egg with the resultant intensity of the 600 mμ light transmitted through the same egg, and if the intensity of the 600 mμ light is considerably reduced the egg is an addled or turbid egg. That is, the phenomenon whereby, when light is transmitted through defective eggs such as those described above, the intensity of the light is greatly reduced is employed for detection of defective eggs.

For inspection of green eggs, 384-mμ light or near-ultraviolet light is applied to an egg to be inspected. If the egg is affected with bacteria, it will luminesce with white color, and if not, its shell will appear to be violet.

Figure 10A:
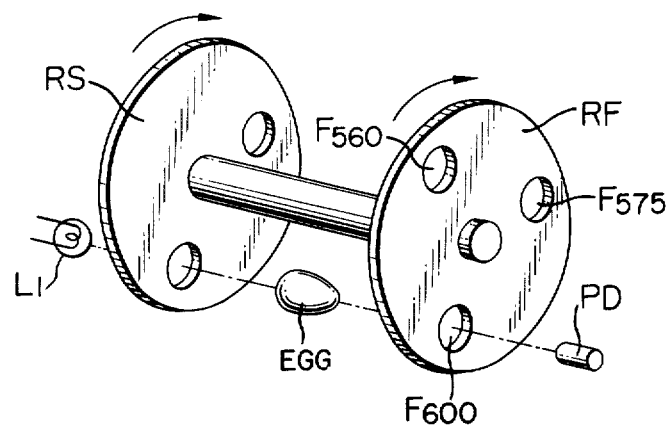
FIG. 10(a) is a perspective view showing an assembly of a rotating shutter and a rotating filter plate employed in the egg inspecting apparatus shown in FIG. 9.

FIGS. 10 (a) and 10(b) indicate the operational and structural relationships between the rotating shutter RS and the rotating filter plate RF. The filter plate RF has three filters F575, F600 and F560 as shown in FIG. 10(a). The filter F575 is adapted to pass a light of 575±2.5-mμ wavelength, while the filter F600 is adapted to pass a light of 600±2.5-mμ wavelength. The filter F560 is constituted by two filters, that is, a UV-38 filter and a Y-50 filter so as to eliminate ultraviolet rays.

The rotating shutter RS, as shown in FIG. 10(a), has two through holes at two positions corresponding to the positions of the filters F575 and F600, but has no hole at a position corresponding to the position of the filter 560.

Figure 10B:
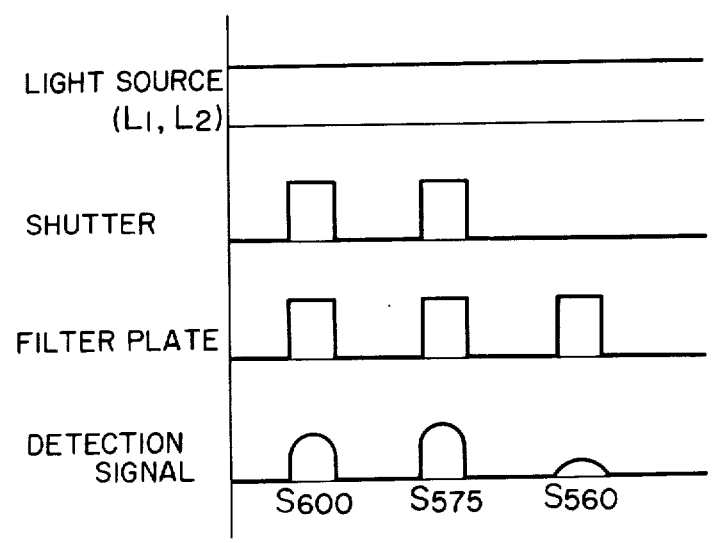
FIG. 10(b) is a diagram for a description of the operation of the assembly shown in FIG. 10(a)

The operation as shown in FIG. 10(b) is carried out with the energization of the motor M. In the case where the light sources $L_1$ and $L_2$ are both turned on, the 600 mμ light and the 575 mμ light are applied through the rotating shutter RS to the photo-sensitive device PD, while the 560 mμ light is not interrupted by the shutter RS as is obvious from FIG. 10(a).

FIG. 11 is a block diagram illustrating the egg inspecting apparatus shown in FIG. 9. An egg to be inspected is placed at the egg inspection point, the light sources $L_1$ and $L_2$ are turned on, and the motor is started. The light from the light source $L_1$ is applied to the egg through the holes of the shutter RS, while the near-ultraviolet rays from the light source $L_2$ are applied directly to the same egg. The lights passed through the filters in the filter plate RF are sequentially applied to the photo-sensitive device PD with the rotation of the filter plate RF.

The lights thus applied are subjected to photoelectric conversion in the photo-sensitive device PD which in turn produces light detection signals, respectively. These light detection signals are introduced into a signal processing section which, as shown in FIG. 11, comprises a synchronization type separator SS, amplifiers $AMP_1$, $AMP_2$ and $AMP_3$, peak holders $PH_1$, $PH_2$ and $PH_3$, a comparator COMP, and level detectors $LD_1$ and $LD_2$. The detection signals thus applied is further distributed as signals $S_{575}$, $S_{600}$ and $S_{650}$ separately to the following stage by the separator SS with the aid of synchronization signals $P_1$, $P_2$ and $P_3$ or timing pulses produced by a timing pulse generator TP. That is, the three signals $S_{575}$, $S_{600}$ and $S_{560}$ are applied to the amplifiers $AMP_1$, $AMP_2$ and $AMP_3$, respectively. The timing pulse generator TP produces the three synchronization signals $P_1$, $P_2$ and $P_3$ in synchronization with the rotation of the shutter RS (or the filter plate RF) when a signal representative of the presence of an egg inspection point is applied thereto.

The signals $S_{575}$, $S_{600}$ and $S_{560}$ are amplified by the amplifiers $AMP_1$, $AMP_2$ and $AMP_3$, and then stored in the peak holders $PH_1$, $PH_2$ and $PH_3$, respectively. The output signals of the peak holders $PH_1$ and $PH_2$ are applied to the comparator COMP. If the signal $S_{575}$ is less than a predetermined value with respect to the signals $S_{600}$, the comparator COMP will produce an output signal at its output terminal $OUT_1$. This means that the intensity of the 575-m$\mu$ light is reduced by the egg more than that of the 600-m$\mu$ light, and that the egg contains blood.

If the output signal of the peak holder $PH_2$ is less than another predetermined value, the level detecto $LD_1$ connected to the peak holder $PH_2$ produces an output signal at its output terminal $OUT_2$. This means that the 600-m$\mu$ light could not be sufficiently transmitted through the egg regardless of blood, that is, the egg is an addled or turbid egg.

Furthermore, if the output signal of the peak holder $PH_3$ is greater than a predetermined value, the level detector $LD_2$ connected to the peak holder $PH_3$ receiving the output signal produces an output signal at its output terminal $OUT_3$. This means that the egg is affected with bacteria and luminesced with white color upon irradiation of the near-ultraviolet ray thereon.

When the shutter RS is rotated further after the egg inspecting operation described above, the timing pulse generator TP produces a reset pulse RP, which is applied to all of the peak holders $PH_1$, $PH_2$ and $PH_3$. As a result, the peak holders $PH_1$, $PH_2$ and $PH_3$ are reset to be ready for the inspection of the succeeding egg.

If there is no egg at the egg inspection point when the lights from the light sources are applied to the photosensitive device PD, the timing pulse generator TP produces no synchronization signals because the signal representative of the presence of an egg at the egg inspection point is not applied to the timing pulse generator TP. As a result, the separator SS is not operated.

Figure 12:
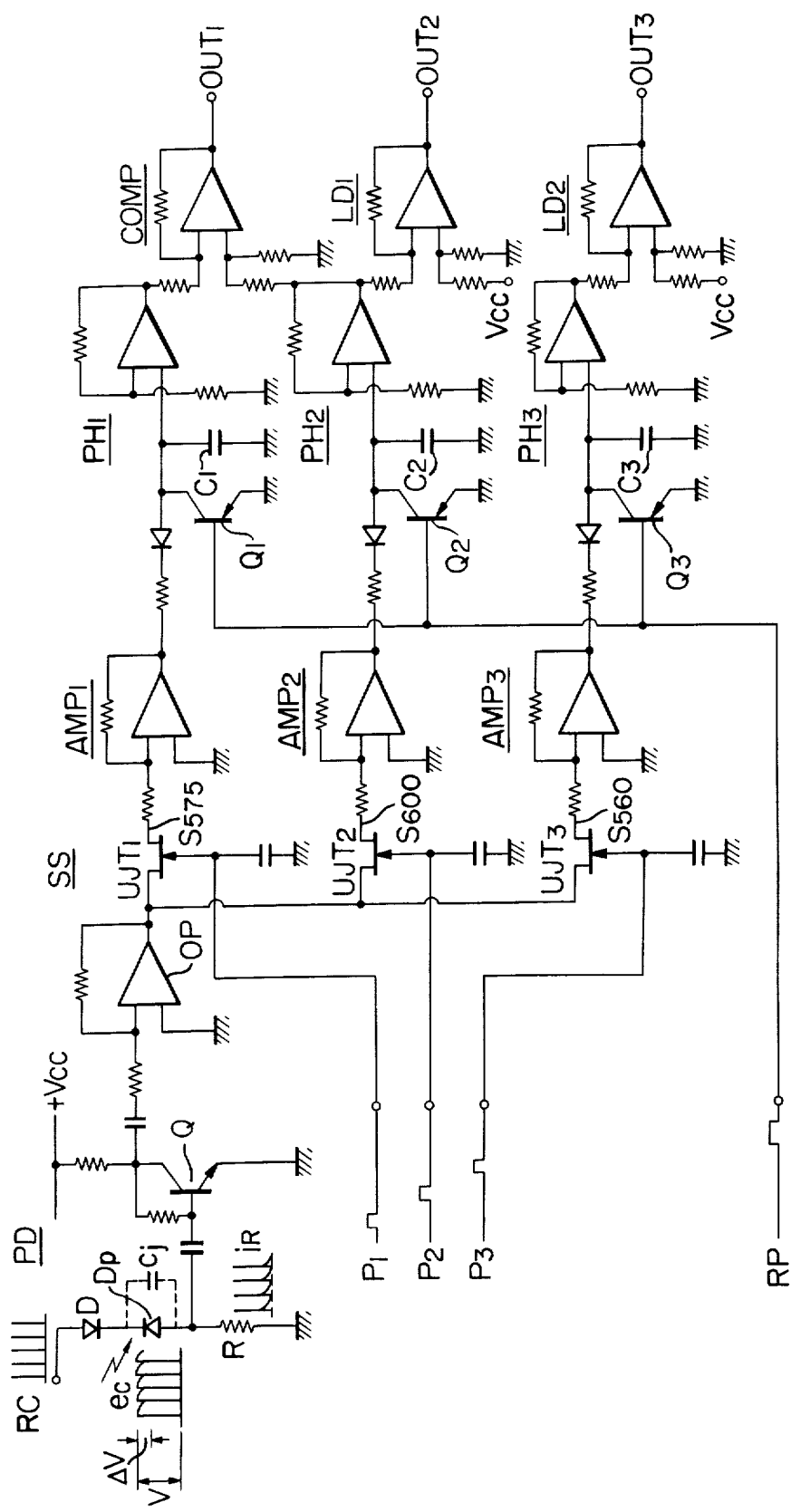
FIG. 12 is an electric circuit diagram of the egg inspecting apparatus shown in FIGS. 9 and 11.

FIG. 12 is an electrical circuit diagram illustrating in detail the block diagram of FIG. 11. As is apparent from the comparison of the circuit diagram of FIG. 12 with that of FIG. 4, the circuit of FIG. 10 can be obtained by adding the circuits of the pulse $P_3$, a unijunction transistor $UJT_3$, the amplifier $AMP_3$, the peak holders $PH_3$, and the level detector $LD_2$ to the circuit of FIG. 4. Therefore, the construction and operation of the photosensitive device PD are the same as those described before, that is, a voltage iR·R, as described before, is developed across the resistor R, is amplified by the transistor Q and the operational amplifier OP, and is applied to the unijunction transistors $UJT_1$, $UJT_2$ and $UJT_3$ of the separator SS.

These unijunction transistor operate as gate circuits which open with the aid of timing pulses $P_1$, $P_2$ and $P_3$ applied to the emitters by the timing pulse generator TP, respectively, so that the signals from the device PD are applied to the amplifiers $AMP_1$, $AMP_2$ and $AMP_3$, respectively. Since the timing pulses are applied to the respective transistors in synchronization with the rotation of the filter plate RF, the voltage signals or output signals of the operational amplifier OP are selectively applied to the respective amplifiers $AMP_1$, $AMP_2$ and $AMP_3$. In other words, the voltage signal produced upon application of the 575-m$\mu$ light is applied to the amplifier $AMP_1$; the voltage signal produced upon application of the 600-m$\mu$ light is applied to the amplifier $AMP_2$; and the voltage signal produced upon application of the near-ultraviolet rays is applied to the amplifier $AMP_3$.

The signals amplified by the amplifiers $AMP_1$, $AMP_2$ and $AMP_3$ are applied to the park holders $PH_1$, $PH_2$ and $PH_3$, respectively. The peak holders $PH_1$, $PH_2$ and $PH_3$ comprise circuits including transistors $Q_1$, $Q_2$ and $Q_3$, respectively. The function of each peak holder is the same as that described with reference to the peak holders $PH_1$ and $PH_2$ in FIG. 4. Briefly described, each peak holder stores the peak value of a signal applied thereto until it is reset by the reset signal RP. When the signals from the amplifier $AMP_1$ and $AMP_2$ are applied to the peak holders $PH_1$ and $PH_2$, respectively, no reset signal is applied to the latter, and the peak holders $PH_1$ and $PH_2$ therefore store the peak values of the signals produced by the amplifiers $AMP_1$ and $AMP_2$ and introduce them to the comparator COMP. The comparator COMP operates in the same manner as described with reference to FIG. 4, and produces an output signal at the output terminal $OUT_1$. This output signal is used to reject a blood-containing egg.

The output signal of the peak holder $PH_2$, as was described before, is further applied to the level detector $LD_1$ in which the level of the non-absorptive light or 600-m$\mu$ light is compared with a predetermined value. If this level is less than the predetermined value, the egg is a black egg, and the level detector $LD_1$ produces an output signal at the output terminal $OUT_2$ to reject the egg.

The output signal of the peak holder $PH_3$ is applied to the level detector $LD_2$ where it is determined whether or not the luminosity of the egg is greater than a predetermined value. If this luminosity is greater than the predetermined value, the egg is a green egg and the level detector $LD_2$ produces an output signal at the output terminal $OUT_3$ to reject the egg.

Figure 13:
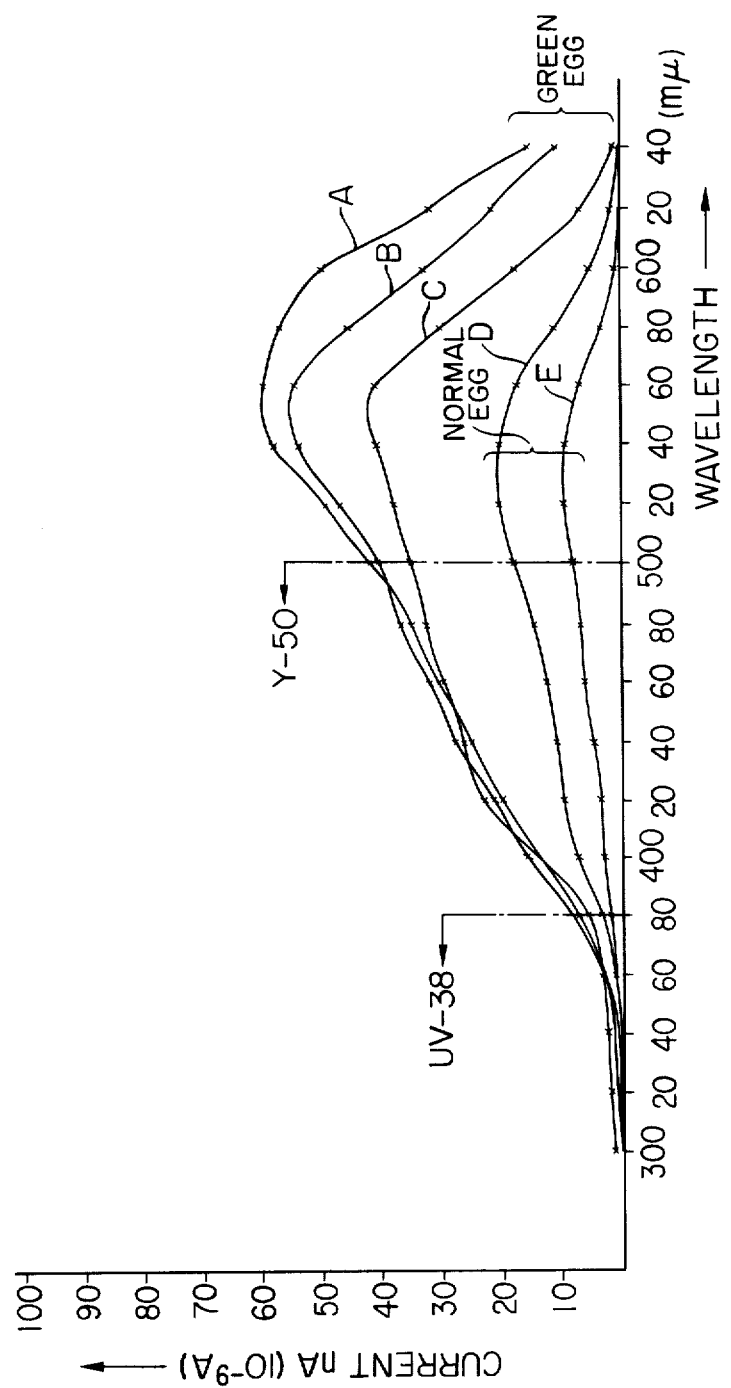
FIG. 13 is a graphical representation indicating characteristic curves plotted by applying light ranging from 300 m$\mu$ to 640 m$\mu$ to normal eggs and eggs affected with bacteria.

As is apparent from FIG. 13, the levels of characteristic curves A, B and C plotted by applying lights ranging from 300 m$\mu$ to 640 m$\mu$ in wavelength to green eggs are clearly different from those of characteristic curves D and E plotted by applying the same lights to normal eggs. This difference is utilized to positively reject green eggs. The characteristic curves of green eggs shown in FIG. 13 are applicable to the inspection of addled or turbid eggs, that is, the characteristic curves of addled or turbid eggs can be estimated from the characteristic curves of green eggs.

The output levels indicated in FIG. 6 are greatly different from those indicated in FIG. 11, for various conditions such as, for instance, the intensity of a light source in the case of FIG. 6 are different from those in the case of FIG. 13.

In the apparatus described above, three different lights are received by one optional detector and are separated by the use of timing pulses. However, this method may be replaced by a method in which three photo-sensitive devices are provided for the three different lights, respectively. Furthermore, the two light sources $L_1$ and $L_2$ may be replaced by one light source which can emit the three different lights in mixed state.

Furthermore, in the third example of the invention described above, the 575-mμ, 600-mμ and 384-mμ lights are employed for the rejection of defective eggs because the 575-mμ and 600-mμ lights are most suitable in view of the optical transmission characteristics of eggs, and the 384-mμ light is superior for detecting the luminescence characteristic of eggs. However, lights of other wavelengths may be employed for the same purpose. Furthermore, the photo-diode in the optical detector may be replaced by a photo-transistor or a solar battery similarly as in the first example of this invention.

Furthermore, the light of blood-sensitive wavelength, the light of blood-nonsensitive wavelength and the near-ultraviolet light are applied to an egg to be inspected, and the lights from the egg are separately subjected to photo-electric conversion by the photo-sensitive device or the dielectric charge storing element, as a result of which three light detection signals are produced. Then, it is determined whether or not the level of the light detection signal produced by the application of the light of a blood-sensitive wavelength is less than a predetermined value with respect to the level of the light detection signal produced by the application of the light having a blood-nonsensitive wavelength. Furthermore, it is determined whether or not the level of the latter light detection signal and the level of the light detection signal produced by the application of the near-ultraviolet rays are compared with predetermined values, respectively. Accordingly, defective eggs can be quickly and positively detected, and the problems accompanying the photomultiplier tube employed in the conventional egg inspecting apparatus can be solved because the electric charge storing element is employed in the photo-sensitive device.

In the case where the different lights are applied to an egg at different time instants as was described above, the detection of these lights can be effected by only one optical detector. On the other hand, in the case where a photo-sensitive device is provided for each of the different lights, the constructions of the light emitting section and the light detection signal processing section can be made simple when compared with the former case.

What is claimed is:

1. An egg inspecting apparatus which comprises:
light emitting means having a light source for projecting through an egg to be inspected a first light having a wavelength which is appreciably absorbed by a content of said egg and a second light having a wavelength which is not appreciably absorbed by said content of the egg;
photo-sensitive means comprising an electric charge storing element for receiving said first and second lights transmitted through said egg to produce first and second detection signals, respectively;
signal processing means for processing said first and second signals to produce an output signal when the level of said first detection signal is less than a first predetermined value with respect to the level of said second detection signal, and to produce an output signal when the level of said second detection signal is smaller than a second predetermined value;
said light emitting means further comprising a rotating filter plate provided with a first filter for passing said first light and a second filter for passing said second light thereby to alternately project said first and second lights through said egg to be inspected to said photo-sensitive means;
said signal processing means comprising:
a synchronization type separator connected to said photo-sensitive means for separately applying said first and second detection signals with the aid of timing pulses produced in synchronization with the rotation of said rotating filter plate respectively to first and second peak holders connected to said separator, said first peak holder storing a peak value of said first detection signal applied thereto, said second peak holder storing a peak value if said second detection signal applied thereto;
a comparator connected to said first and second peak holders for comparing outputs produced respectively by said first and second peak holders thereby to produce an output signal when the level of the output of said first peak holder is less than a first predetermined value with respect to the level of the output of said second peak holder; and
a level detector connected to said second peak holder for receiving the output of said second peak holder, said level detector producing an output signal when the level of the output of said second peak holder is less than a second predetermined value.

2. An egg inspecting apparatus which comprises:
light emitting means having a light source for projecting through an egg to be inspected a first light having a wavelength which is appreciably absorbed by a content of said egg and a second light having a wavelength which is not appreciably absorbed by said content of the egg;
photo-sensitive means comprising an electric charge storing element for receiving said first and second lights transmitted through said egg to produce first and second detection signals, respectively;
signal processing means for processing said first and second signals to produce an output signal when the level of said first detection signal is less than a first predetermined value with respect to the level of said second detection signal, and to produce an output signal when the level of said second detection signal is smaller than a second predetermined value;
said light emitting means further comprising a second light source for applying to said egg a third light having a wavelength which causes an egg affected with bacteria to produce fluorescent light which is received by said photo-sensitive means to produce a third detection signal;
said signal processing means further comprising means for producing an output signal when the level of said fluorescent light is greater than a third predetermined value;
said light emitting means further comprising a rotating filter plate provided with three filters for respectively passing said first and second light transmitted through said egg and said fluorescent light from the egg thereby to successively applying said three different lights to said photo-sensitive means;
said signal processing means comprising:
a synchronization type separator connected to said photo-sensitive means for separately applying first, second and third detection signals with the aid of timing pulses produced in synchronization with the rotation of said rotating filter plate respectively to first, second and third peak holders connected to said synchronization type separator, said first peak holder storing a peak value of said first detection signal, said second peak holder storing a peak value of said second detection signal, said third peak holder storing a peak value of said third detection signal, a comparator connected to said first and second peak holders for comparing outputs produced respectively by said first and second peak holders thereby to produce an output signal when the level of the output of said first peak holder is less than a first perdetermined value with respect to the level of the output of said second peak holder;

a first level detector connected to said second peak holder for receiving the output of said second peak holder, said level detector producing an output signal when the level of the output of said second peak holder is less than a second predetermined value;

a second value detector connected to said third peak holder for receiving an output of said third peak holder, said second level detector producing an output signal when the level of the output of said third peak holder is greater than a third predetermined value.

* * * * *